US009662596B2

(12) United States Patent
Jones et al.

(10) Patent No.: US 9,662,596 B2
(45) Date of Patent: May 30, 2017

(54) POLYMER-BASED EMULSION BREAKING METHODS

(71) Applicant: LIFE TECHNOLOGIES CORPORATION, Carlsbad, CA (US)

(72) Inventors: Ryan Jones, New Haven, CT (US); Maximilian Carpino, Guilford, CT (US)

(73) Assignee: LIFE TECHNOLOGIES CORPORATION, Carlsbad, CA (US)

(*) Notice: Subject to any disclaimer, the term of this patent is extended or adjusted under 35 U.S.C. 154(b) by 155 days.

(21) Appl. No.: 14/528,138

(22) Filed: Oct. 30, 2014

(65) Prior Publication Data

US 2015/0057377 A1   Feb. 26, 2015

Related U.S. Application Data

(63) Continuation of application No. PCT/US2013/031097, filed on Mar. 13, 2013.

(60) Provisional application No. 61/640,258, filed on Apr. 30, 2012.

(51) Int. Cl.
| | | |
|---|---|---|
| *B01D 17/04* | (2006.01) | |
| *C12Q 1/68* | (2006.01) | |
| *C10G 33/04* | (2006.01) | |
| *C07H 21/00* | (2006.01) | |
| *B01D 21/00* | (2006.01) | |

(52) U.S. Cl.
CPC ....... *B01D 17/047* (2013.01); *B01D 21/0009* (2013.01); *C07H 21/00* (2013.01); *C10G 33/04* (2013.01); *B01D 21/00* (2013.01); *C12Q 1/68* (2013.01)

(58) Field of Classification Search
CPC .. B01D 17/047; B01D 21/00; B01D 21/0009; C07H 21/00; C10G 33/04; C12Q 1/68; C12Q 1/686; C12Q 1/6844; C12Q 1/6869
See application file for complete search history.

(56) References Cited

U.S. PATENT DOCUMENTS

| | | | |
|---|---|---|---|
| 6,627,603 B1 | 9/2003 | Bibette et al. | |
| 7,604,940 B1* | 10/2009 | Voss | C12Q 1/6869 435/6.16 |
| 8,168,062 B2* | 5/2012 | McDaniel | B01D 17/047 208/188 |
| 2011/0086780 A1* | 4/2011 | Colston, Jr. | B01F 3/0807 506/23 |
| 2011/0087016 A1 | 4/2011 | Suo | |
| 2011/0217712 A1* | 9/2011 | Hiddessen | C12Q 1/6846 435/6.12 |
| 2011/0253598 A1* | 10/2011 | McDaniel | B01D 17/047 208/188 |
| 2014/0080717 A1* | 3/2014 | Li | C12Q 1/6855 506/2 |

FOREIGN PATENT DOCUMENTS

EP    2377910    10/2011

OTHER PUBLICATIONS

Williams et al., Amplification of complex gene libraries by emulsion PCR, Nature Methods, vol. 3, No. 7, (Jul. 2006), pp. 545-550.*
Schutze et al., A streamlined protocol for emulsion polymerase chain reaction and subsequent purification, Analytical Biochemistry 410 (2011)155-157.*
International Preliminary Amendment on Patentability for International Application No. PCT/US2013/031097 mailed Nov. 4, 2014, 6 pages.
International Search Report of the International Searching Authority and Written Opinion for International Application No. PCT/US2013/031097 mailed Sep. 4, 2013, 10 pages.

* cited by examiner

*Primary Examiner* — Daniel S Metzmaier

(57) ABSTRACT

A method for breaking emulsions includes applying a polymer mixture to an emulsion. The emulsion can be energized, such as through centrifugation or vibration. In particular, the polymer mixture can be in liquid form. The polymer mixture includes first and second liquid polymer, the second liquid polymer being less hydrophilic than the first liquid polymer. Example polymer useful as the first or second liquid polymers includes polyether. In a water-in-oil emulsion, the less hydrophilic polymer can preferentially reside within the oil phase.

10 Claims, No Drawings

POLYMER-BASED EMULSION BREAKING METHODS

CROSS-REFERENCE TO RELATED APPLICATION(S)

This application is a continuation of PCT Application No. PCT/US/2013/031097, which claims benefit of U.S. Provisional Application No. 61/640,258, filed Apr. 30, 2012, which are incorporated herein by reference in their entirety.

FIELD OF THE DISCLOSURE

This disclosure, in general, relates to methods for breaking emulsion's using polymer-based solutions.

BACKGROUND

Various chemical and molecular biology techniques use emulsions to provide isolated volumes of reactants. For example, in polymerization techniques, emulsions are used in emulsion polymerization and high internal phase emulsion (HIPE) polymerization to provide limited volumes in which polymerization occurs. In molecular biology, emulsions are used in emulsion polymerase chain reactions (PCR) to provide isolated volumes in which PCR can occur. In particular, methods of forming particles enhanced with copies of target polynucleotides can utilize emulsions to encouraging a 1:1 ratio of the target polynucleotide and a polymeric particle within an isolated volume, thus producing a polymeric particle that includes copies of one target polynucleotide.

In such techniques, once the reaction has taken place, the emulsion is broken to collect the products of the reaction. In particular, the emulsion is broken and the phases are separated to allow for separation of the desired reaction products that reside within one of the phases.

However, conventional emulsion breaking techniques either utilize volatile organic compounds or utilize sulfonate surfactants. Volatile organic compounds, such as butanol, are flammable and can be irritants to users. As such, when volatile organic compounds are utilized to break emulsion, such emulsion breaking is performed in a hood, limiting access to the emulsion and increasing the cost of such emulsion breaking techniques. In general, sulfonate-based emulsion breaking techniques are less effective than the volatile organic compound techniques, frequently resulting in incomplete separation of the reaction products.

SUMMARY

In an aspect, a method of recovering a particle from an emulsion includes contacting the emulsion with a breaking solution. The emulsion includes an aqueous phase dispersed in an immiscible continuous phase. The aqueous phase includes hydrophilic particles. The breaking solution includes a first liquid polymer and a second liquid polymer. The first liquid polymer has affinity for the aqueous phase, and the second liquid polymer has affinity for the immiscible continuous phase. The molecular weight of the first liquid polymer is less than the molecular weight of the second liquid polymer. The contacting breaks the emulsion, providing a continuous aqueous phase including the hydrophilic particles. The method further includes separating the immiscible continuous phase from the continuous aqueous phase.

In a second aspect, a kit includes a breaking solution comprising a first liquid polymer and a second liquid polymer. The molecular weight of the first liquid polymer is less than the molecular weight of the second liquid polymer. The kit further includes a hydrophilic polymer particle solution and a water-immiscible fluid. The first liquid polymer has affinity for an aqueous phase and the second liquid polymer has affinity for the water-immiscible fluid.

DESCRIPTION OF THE PREFERRED EMBODIMENT(S)

In an exemplary embodiment, a method for breaking emulsions includes applying a polymer mixture to an emulsion. The emulsion can be energized, such as through centrifugation or vibration. In particular, the polymer mixture can be in liquid form. The polymer mixture includes a first liquid polymer and includes a second liquid polymer. The second liquid polymer is less hydrophilic than the first liquid polymer. For example, at an oil-water system, the second liquid polymer can preferentially reside within the oil phase, such as in the oil phase at the oil-water interface.

In another exemplary embodiment, a kit can include polymers useful in breaking emulsions. The kit can include a mixture of polymers for breaking an emulsion. The mixture can be in liquid form. In particular, the mixture includes a first liquid polymer and a second liquid polymer. The second liquid polymer can have affinity for and preferentially reside within a water immiscible phase following emulsion breaking. The kit can also include components for performing the emulsion-based reaction, such as a solution to form a continuous phase, e.g., a solution that is immiscible with water when a water-in-oil emulsion is formed. In addition, the kit can include one or more aqueous solutions including reactive components. In an emulsion PCR kit, one or more solutions can include enzymes and nucleotides, as well as other cofactors, useful in amplifying polynucleotides, such as through polymerase chain reaction (PCR). When coupling the amplified copies of target polynucleotides to a polymeric particle, an aqueous solution including polymeric particles can also be included in the kit.

In an exemplary embodiment, a mixture of polymers is utilized to break an emulsion. The mixture includes a first liquid polymer, a second liquid polymer, and optionally, a third liquid polymer. The first liquid polymer has affinity for aqueous phases and preferentially resides in aqueous phases in a multiphase system, for example, within the aqueous phase at an oil-water interface. The second liquid polymer is less hydrophilic and can preferentially reside in a water-immiscible phase.

The first liquid polymer can include a polyether, such as a low molecular weight polyether. In particular, the polyether can be formed from monomers that include not greater than two carbons. In particular, an exemplary polyether can include polyethylene glycol, polyoxymethylene, or any combination thereof.

The first liquid polymer can be in liquid form and can have a low molecular weight. For example, the first liquid polymer can have a molecular weight in a range of 50 to 500 Da, such as a range of 100 to 400 Da, a range of 100 to 300 Da, or even a range of 150 to 250 Da, in particular approximately 200 Da.

A second liquid polymer is less hydrophilic than the first liquid polymer. In particular, the second liquid polymer can preferentially reside within an oil phase following emulsion breaking. Optionally, the second liquid polymer is hydrophobic. An exemplary second liquid polymer can be polyether formed of monomers having at least three carbons. For example, the second liquid polymer can include polypropylene glycol, polytetramethylene glycol, fluorinated polyethers, or any combination thereof.

The second liquid polymer can be in liquid form and can have a higher molecular weight than the first liquid polymer. For example, the second liquid polymer can have a molecular weight in a range of 100 Da to 700 Da, such as a range of 200 Da to 600 Da, a range of 300 Da to 600 Da, or even a range of 400 Da to 500 Da, or approximately 475 Da.

A third liquid polymer can be included. The third liquid polymer can include polypropylene glycol, polytetramethylene glycol, fluorinated polyethers, or any combination thereof. In an example, the third liquid polymer can have a molecular weight that is greater than the molecular weights of the first and second liquid polymers. For example, the third liquid polymer can have a molecular weight in a range of 1000 Da to 5000 Da, such as a range of 1200 Da to 4000 Da, a range of 1500 Da to 3000 Da, or even a range of 1500 Da to 2500 Da, or approximately 2000 Da. The third liquid polymer can be used in a ratio of 1:50 to 1:2 (third liquid polymer:second liquid polymer), such as a range of 1:10 to 1:3, a range of 1:10 to 1:5, a range of 1:7 to 1:5, or approximately 1:6.

In a particular example, the polymers are mixed in an emulsion breaking solution. Optionally, the emulsion breaking solution includes an aqueous base. The total amount of polymer include an emulsion breaking solution can be as high as 100 vol %. Alternatively, the total amount of polymer in the emulsion breaking solution can be in a range of 10 vol % to 100 vol %, such as a range of 25 vol % to 95 vol %, a range of 50 vol % to 95 vol %, or even a range of 75 vol % to 95 vol %.

The mixture of polymers within the polymer breaking solution can be included in a ratio of the second liquid polymer (or a blend of the second liquid polymer and a third liquid polymer) to the first liquid polymer (second liquid polymer:first liquid polymer) of 1:3 to 10:1, such as in a range of 1:2 to 7:1, a range of 1:1 to 5:1, a range of 2:3 to 4:1, or even approximately 7:2.

In particular, the polymer breaking solution can include water, e.g., provided as deionized water. The polymer breaking solution can also include other factors, such as surfactants, pH buffers, or ionic components. In particular, the polymer breaking solution is free of low boiling solvents, such as solvents having a normal boiling point not greater than the normal boiling point of water. Moreover, the emulsion breaking process can be performed without such low boiling solvents.

In an example, the polymer breaking solution can include not greater than 1% of a surfactant other than the above polymers, such as not greater than 0.5 wt %, not greater than 0.2 wt %, or even not greater than 0.1 wt %. The surfactant can be an ionic surfactant, an amphoteric surfactant, or a non-ionic surfactant. The ionic surfactant can be an anionic surfactant. In another example, the ionic surfactant can be a cationic surfactant. An exemplary anionic surfactant includes a sulfate surfactant, a sulfonate surfactant, a phosphate surfactant, a carboxylate surfactant, or any combination thereof. An exemplary sulfate surfactant includes alkyl sulfates, such as ammonium lauryl sulfate, sodium lauryl sulfate (sodium dodecyl sulfate, (SDS)), or a combination thereof; an alkyl ether sulfate, such as sodium laureth sulfate, sodium myreth sulfate, or any combination thereof; or any combination thereof. An exemplary sulfonate surfactant includes an alkyl sulfonate, such as sodium dodecyl sulfonate; docusates such as dioctyl sodium sulfosuccinate; alkyl benzyl sulfonate; or any combination thereof. An exemplary phosphate surfactant includes alkyl aryl ether phosphate, alkyl ether phosphate, or any combination thereof. An exemplary carboxylic acid surfactant includes alkyl carboxylates, such as fatty acid salts or sodium stearate; sodium lauroyl sarcosinate; a bile acid salt, such as sodium deoxycholate; or any combination thereof. In particular, the surfactant is SDS.

An exemplary cationic surfactant includes primary, secondary or tertiary amines, quaternary ammonium surfactants, or any combination thereof. An exemplary quaternary ammonium surfactant includes alkyltrimethylammonium salts such as cetyl trimethylammonium bromide (CTAB) or cetyl trimethylammonium chloride (CTAC); cetylpyridinium chloride (CPC); polyethoxylated tallow amine (POEA); benzalkonium chloride (BAC); benzethonium chloride (BZT); 5-bromo-5-nitro-1,3-dioxane; dimethyldioctadecylammonium chloride; dioctadecyldimethylammonium bromide (DODAB); or any combination thereof.

An exemplary amphoteric surfactant includes a primary, secondary, or tertiary amine or a quaternary ammonium cation with a sulfonate, carboxylate, or phosphate anion. An exemplary sulfonate amphoteric surfactant includes (3-[(3-cholamidopropyl)dimethylammonio]-1-propanesulfonate); a sultaine such as cocamidopropyl hydroxysultaine; or any combination thereof. An exemplary carboxylic acid amphoteric surfactant includes amino acids, imino acids, betaines such as cocamidopropyl betaine, or any combination thereof. An exemplary phosphate amphoteric surfactant includes lecithin.

In a particular example, the emulsion breaking solutions can be utilized in a process to form particles including copies of target polynucleotides that are to be positioned on sensor arrays and utilized for sequencing or genotyping such target polynucleotides.

In an exemplary method, a sample solution including a set of target polynucleotides is provided. In addition, reagent solutions can include a solution including a dispersion of particles and a solution that is immiscible with aqueous solutions. The particle can include a hydrophilic polymer particle, such as a hydrogel particle. For example, the hydrophilic polymer particle can include acrylate, polyether, polyacrylamide, copolymers thereof, derivatives thereof, or combinations thereof. In an example, the hydrophilic polymer particle can be conjugated with an oligonucleotide primer. An exemplary immiscible solution includes an oil. In addition, the system can include a reagent solution that includes enzymes, nucleotides, and various chemicals and cofactors useful in polynucleotide amplification, such as polymerase chain reaction (PCR). Alternatively, such enzymes and other components can be incorporated into the solution that includes the particles.

The particle solution, sample solution, optional component solution and the immiscible solution can be provided to an emulsion generating device. In an example, the emulsion generating device is a mechanical emulsion generating device, such as an IKA Turrax device. In another example, the emulsion generating device includes a membrane and set of channel gaskets to generate an emulsion by flowing a mixture through channels of the channel gasket, back and forth through a membrane. In another example, the emulsion can be generated by a pipetting system oscillating immiscible solutions back-and-forth through a pipette tip to generate aqueous emulsion droplets within an immiscible continuous phase. In an example, the continuous phase can comprise a mineral oil such as Petroleum Special, an alkane such as heptadecane, a halogenated alkane such as bromohexadecane, an alkylarene, a halogenated alkyarene, a carbonate oil (e.g., Tegosoft DEC™), an ether, or an ester having a boiling temperature above 100° C., or any combination thereof. The carrier fluid can be insoluble or only slightly soluble in water. The ratio between the carrier fluid and the discrete aqueous phase can range, for example, from 1/0.1 v/v to 4/1 v/v, from 0.5/1 to 3/1, from 0.8/1 to 1/1, or as desired.

In an example, the emulsion can be distributed among tubes or wells over a thermocycling device. The temperature of the emulsion can be controlled to facilitate amplification, e.g., cycled to facilitate PCR. As a result, particles within the emulsion droplets can be conjugated with copies of target polynucleotides to form polynucleotide particles.

The emulsion can be broken by applying emulsion breaking reagents to the emulsion. The emulsion can further be broken using a centrifuge apparatus or through vibration. In another example, emulsion breaking solutions can include polymer species operable to facilitate phase separation. In particular, the emulsion breaking solution includes a first liquid polymer, a second liquid polymer, and a third liquid polymer. The second liquid polymer and the third liquid polymer have affinity for the immiscible phase and preferentially reside in the water-immiscible phase following the breaking of the emulsion, for example, in an oil phase at least partially at the oil-water interface. Such phase separation can be further encouraged by centrifugation or vibration.

In a particular example, the emulsion breaking solution is provided with the emulsion in a volume ratio in a range of 20:1 to 1:10 (emulsion breaking solution:emulsion), such as a range of 15:1 to 1:5, a range of 15:1 to 1:1, or even a range of 15:1 to 5:1. For example, when the emulsion has a volume in a range of 10 microliters to 1 mL, the emulsion breaking solution can be provided in a volume in a range of 1 mL to 20 mL.

Once the emulsion is broken, the oil phase can be separated from the aqueous phase. The aqueous phase includes polynucleotide particles that include multiple copies of target polynucleotides.

Optionally, the particle solution can be further enriched to remove particles that do not include copies of the target polynucleotides. In an example, particles that include copies of the polynucleotides can be coupled with magnetic particles. The solution including the particles coupled to the magnetic particles can be moved to a position adjacent a magnet. Those particles coupled to the magnetic particles can be secured within a tube adjacent to the magnet, while other particles not secured to the magnetic particles can be flushed or washed from the tube using a washing reagent solution. Following washing, the magnet can be moved or the tube can be moved from adjacent the magnet, releasing the magnetic particles. The particles coupled to the magnetic particles can be detached from contact with magnetic particles using chemical methods. The magnet can be used to secure the magnetic particles, which are not coupled to polynucleotide particles. A solution including the polynucleotide particles can be removed and can be loaded onto an array of sensors.

In an example, the solution including polynucleotide particles can be applied over the array. The solution can be applied in a single aliquot or can be applied in partial aliquots followed by centrifugation. In an example, the array can be formed of a substrate that is placed within a tray on the centrifuge. Following each application of an aliquot of the solution including polynucleotide particles, the substrate can be centrifuged to facilitate deposition of the particles on the array.

The above polymer-based emulsion breaking technique provides advantageous technical features including the breaking of emulsion without using volatile organic compounds or without utilizing chemical reagents that can interfere with use of the reaction products, such as the use of polymeric particles including copies of target polynucleotides in sequencing methods.

In an aspect, a method of recovering a particle from an emulsion includes contacting the emulsion with a breaking solution. The emulsion includes an aqueous phase dispersed in an immiscible continuous phase. The aqueous phase includes hydrophilic particles. The breaking solution includes a first liquid polymer and a second liquid polymer. The first liquid polymer has affinity for the aqueous phase, and the second liquid polymer has affinity for the immiscible continuous phase. The molecular weight of the first liquid polymer is less than the molecular weight of the second liquid polymer. The contacting breaks the emulsion, providing a continuous aqueous phase including the hydrophilic particles. The method further includes separating the immiscible continuous phase from the continuous aqueous phase.

In an example of the aspect, the breaking solution has a total polymer content in a range of 10% to 100% by volume. For example, the total polymer content is in a range of 50% to 95% by volume.

In another example of the aspect and the above example, the breaking solution includes the first liquid polymer and the second liquid polymer in a ratio of 1:3 to 10:1 (second liquid polymer:first liquid polymer). For example, the ratio is in a range of 1:1 to 5:1.

In a further example of the aspect and the above examples, the first liquid polymer has a molecular weight in a range of 50 Da to 500 Da. For example, the molecular weight is in a range of 100 Da to 300 Da.

In an additional example of the aspect and the above examples, the second liquid polymer has a molecular weight in a range of 100 Da to 700 Da. For example, the second liquid polymer has a molecular weight in a range of 300 Da to 600 Da.

In another example of the aspect and the above examples, the emulsion is contact with the breaking solution in a ratio in a range of 20:1 to 1:10. For example, the ratio is in a range of 15:1 to 1:1.

In a further example of the aspect and the above examples, the first liquid polymer comprises polyether. For example, the polyether includes polyethylene glycol, polyoxymethylene, or a combination thereof.

In an additional example of the aspect and the above examples, the second liquid polymer comprises a polyether formed of monomers having at least three carbons. For example, the second liquid polymer comprises include polypropylene glycol, polytetramethylene glycol, fluorinated polyethers, or any combination thereof.

In another example of the aspect and the above examples, the breaking solution further includes a third liquid polymer having a molecular weight greater than the second liquid polymer and having affinity for the immiscible continuous phase. In an example, the third liquid polymer has a molecular weight in a range of 1000 Da to 5000 Da. In another example, the third liquid polymer comprises a polyether formed of monomers having at least three carbons. In a particular example, the third polymer is included in the breaking solution in a ratio relative to the second polymer in a range of 1:50 to 1:2 (third liquid polymer:second liquid polymer).

In a further example of the aspect and the above examples, the hydrophilic particles are polynucleotide particles.

In an additional example of the aspect and the above examples, contacting includes centrifuging. In another example of the aspect and the above examples, contacting includes vibration.

In a second aspect, a kit includes a breaking solution comprising a first liquid polymer and a second liquid polymer. The molecular weight of the first liquid polymer is less than the molecular weight of the second liquid polymer. The kit further includes a hydrophilic polymer particle solution and a water-immiscible fluid. The first liquid polymer has affinity for an aqueous phase and the second liquid polymer has affinity for the water-immiscible fluid.

In an example of the second aspect, the kit further includes a nucleotide solution comprising nucleotides.

In another example of the second aspect and the above examples, the breaking solution has a total polymer content in a range of 10% to 100% by volume.

In a further example of the second aspect and the above examples, the breaking solution includes the first liquid polymer and the second liquid polymer in a ratio of 1:3 to 10:1 (second liquid polymer: first liquid polymer).

In an additional example of the second aspect and the above examples, the first liquid polymer has a molecular weight in a range of 50 Da to 500 Da.

In another example of the second aspect and the above examples, the second liquid polymer has a molecular weight in a range of 100 Da to 700 Da.

In a further example of the second aspect and the above examples, the first liquid polymer comprises polyether. For example, the polyether includes polyethylene glycol, polyoxymethylene, or a combination thereof.

In an additional example of the second aspect and the above examples, the second liquid polymer comprises a polyether formed of monomers having at least three carbons. For example, the second liquid polymer comprises include polypropylene glycol, polytetramethylene glycol, fluorinated polyethers, or any combination thereof.

In another example of the second aspect and the above examples, the breaking solution further comprises a third liquid polymer having a molecular weight greater than the second liquid polymer and having affinity for the immiscible continuous phase. For example, the third liquid polymer has a molecular weight in a range of 1000 Da to 5000 Da. In another example, the third liquid polymer comprises a polyether formed of monomers having at least three carbons. In a particular example, the third polymer is included in the breaking solution in a ratio relative to the second polymer in a range of 1:50 to 1:2 (third liquid polymer:second liquid polymer).

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A method of recovering a particle from an emulsion, the method comprising:

contacting the emulsion with a breaking solution, the emulsion comprising an aqueous phase dispersed in an immiscible continuous phase, the aqueous phase including hydrophilic particles including conjugated copies of a target polynucleotide, the breaking solution comprising a first liquid polymer and a second liquid polymer, the first liquid polymer having affinity for the aqueous phase and the second liquid polymer having affinity for the immiscible continuous phase, wherein the first liquid polymer is polyethylene glycol, polyoxymethylene, or a combination thereof, and has a molecular weight in a range of 50 Da to 500 Da, the second liquid polymer is polypropylene glycol, polytetramethylene glycol, fluorinated polyethers, or any combination thereof, and has a molecular weight in a range of 100 Da to 700 Da, the molecular weight of the first liquid polymer being less than the molecular weight of the second liquid polymer, and wherein the contacting breaks the emulsion, providing a continuous aqueous phase including the hydrophilic particles; and separating the immiscible continuous phase from the continuous aqueous phase.

2. The method of claim 1, wherein the breaking solution has a total polymer content in a range of 10% to 100% by volume.

3. The method of claim 1, wherein the breaking solution includes the first liquid polymer and the second liquid polymer in a ratio of 1:3 to 10:1 (second liquid polymer: first liquid polymer).

4. The method of claim 1, wherein the emulsion is contact with the breaking solution in a ratio in a range of 20:1 to 1:10.

5. The method of claim 1, wherein the breaking solution further comprises a third liquid polymer having a molecular weight greater than the second liquid polymer and having affinity for the immiscible continuous phase.

6. The method of claim 1, wherein contacting includes centrifuging.

7. A kit comprising:
a first reagent solution including an aqueous dispersion of hydrophilic polymer particles;
a second reagent solution immiscible with the first reagent solution; and
a breaking solution comprising a first liquid polymer and a second liquid polymer,
wherein the first liquid polymer is polyethylene glycol, polyoxymethylene, or a combination thereof and has a molecular weight in a range of 50 Da to 500 Da, the second liquid polymer is polypropylene glycol, polytetramethylene glycol, fluorinated polyethers, or any combination thereof and has a molecular weight in a range of 100 Da to 700 Da, the molecular weight of the first liquid polymer being less than the molecular weight of the second liquid polymer, and
wherein the first liquid polymer having affinity for an aqueous phase and the second liquid polymer having affinity for the water-immiscible fluid.

8. The kit of claim 7, further comprising an aqueous nucleotide solution comprising nucleotides.

9. The kit of claim 7, wherein the breaking solution has a total polymer content in a range of 10% to 100% by volume.

10. The kit of claim 7, wherein the breaking solution includes the first liquid polymer and the second liquid polymer in a ratio of 1:3 to 10:1 (second liquid polymer: first liquid polymer).

* * * * *